United States Patent [19]

Nunez

[11] Patent Number: 5,601,599
[45] Date of Patent: Feb. 11, 1997

[54] FLEXIBLE SURGICAL INSTRUMENTS INCORPORATING A HOLLOW LUMEN COIL HAVING AREAS OF DIFFERENT PRELOAD TENSION

[75] Inventor: George Nunez, Miami, Fla.

[73] Assignee: Symbiosis Corporation, Miami, Fla.

[21] Appl. No.: 311,141

[22] Filed: Sep. 23, 1994

[51] Int. Cl.$^6$ ............................. A61B 17/28; A61B 10/00
[52] U.S. Cl. ............................................. 606/205; 128/756
[58] Field of Search ..................................... 606/205, 159, 606/170, 167, 174; 128/751, 752, 657, 772, 749, 750, 753–759

[56] References Cited

U.S. PATENT DOCUMENTS

| | | |
|---|---|---|
| 3,749,085 | 7/1973 | Wilson et al. . |
| 4,080,706 | 3/1978 | Heilman et al. . |
| 4,669,172 | 6/1987 | Petruzzi . |
| 4,936,312 | 6/1990 | Tsukagoshi ........................ 128/749 |
| 4,982,727 | 1/1991 | Sato . |
| 5,092,534 | 3/1992 | Tanaka . |
| 5,103,543 | 4/1992 | Hodgso . |
| 5,108,411 | 4/1992 | McKenzie ............................. 606/159 |
| 5,154,705 | 10/1992 | Fleischhacker et al. ................ 604/282 |
| 5,165,421 | 11/1992 | Fleischhacker et al. ................ 128/772 |
| 5,171,383 | 12/1992 | Sagaye et al. . |
| 5,228,451 | 7/1993 | Bales et al. ............................. 128/751 |
| 5,419,339 | 5/1995 | Palmer ................................... 128/751 |

*Primary Examiner*—Glenn Dawson
*Attorney, Agent, or Firm*—David P. Gordon

[57] ABSTRACT

A hollow lumen coil for a surgical instrument is made from a continuous helically wound filament which is wound with different preload tension at different portions of the coil. When a relatively high preload tension is applied to the filament as the coil is wound, the coil will be relatively stiff. When a relatively low preload tension is applied to the filament as the coil is wound, the coil will be relatively flexible. By varying the preload tension applied to the filament while winding the coil, the coil is provided with areas of different stiffness and flexibility. The preload tension may be varied gradually or abruptly and may be varied several times along the length of the coil. Surgical instruments incorporating the coil are also disclosed. The coil is preferably made from stainless steel Type 304 wire having a diameter of approximately 0.021 inches and is wound with tensions ranging from nil to several pounds.

8 Claims, 3 Drawing Sheets

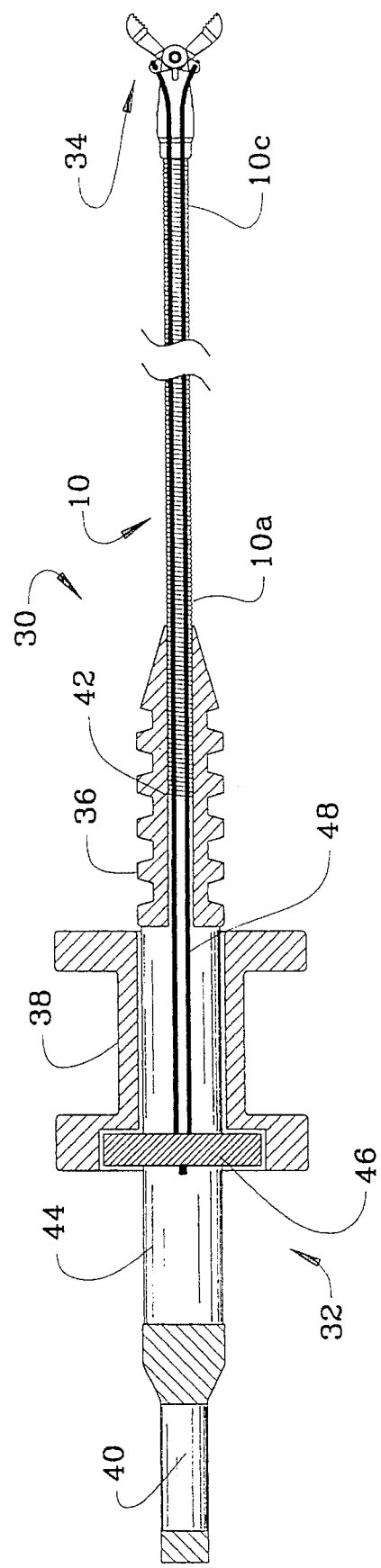
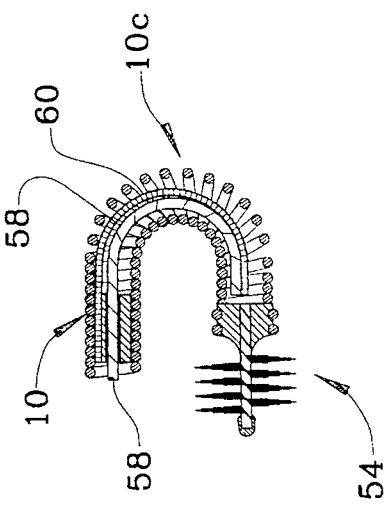
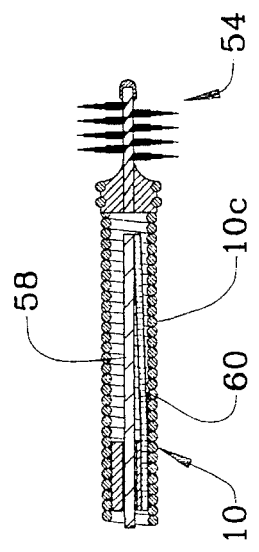

FLEXIBLE SURGICAL INSTRUMENTS INCORPORATING A HOLLOW LUMEN COIL HAVING AREAS OF DIFFERENT PRELOAD TENSION

This application is related to co-assigned application Ser. No. 08/180,649 filed Jan.13, 1994, now U.S. Pat. No. 5,419,339 . This application is also related to co-assigned U.S. Pat. No. 5,228,451 to Bales et al., the complete disclosures of which are hereby incorporated by reference herein.

BACKGROUND OF THE INVENTION

1. Field of the Invention

The invention relates to flexible surgical instruments incorporating a hollow lumen coil. More particularly, the invention relates to a surgical instrument with a hollow lumen coil having areas of different preload tension to effect areas of different stiffness and flexibility in the coil, and to methods for imparting different preload tension to the coil.

2. State of the Art

Flexible surgical instruments, in particular endoscopic biopsy forceps and tissue scrapers, are used for taking tissue samples from the human body for analysis. These instruments typically have a long flexible hollow lumen coil containing one or more control wires coupled to a proximal actuating handle which moves the control wires relative to the coil to effect a tissue sampling operation at the distal end of the coil. In biopsy forceps devices, a pair of forceps jaws are mounted on a clevis at the distal end of the coil and coupled to the one or more control wires so that movement of the control wires causes the jaws to open and close to bite a tissue sample. In biopsy tissue scrapers, a brush or scraping tool is attached to the distal end of the coil and the control wire flexes the distal end of the coil to cause the scraping of a tissue sample.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps or tissue scraper. The practitioner guides the endoscope to the biopsy site while looking through the optical lens and inserts the biopsy forceps or tissue scraper through the lumen of the endoscope to the biopsy site. While viewing the biopsy site through the optical lens of the endoscope, the practitioner manipulates the actuating handle to effect a tissue sampling operation at the distal end of the instrument. In the case of biopsy forceps, the practitioner must align the open jaws with the tissue to be sampled so that upon closing the jaws, a portion of the tissue is trapped between the jaws. It is a known problem with biopsy forceps that as the jaws are closed the distal end of the flexible coil deflects because the force applied at the actuating handle to the control wires is transferred to the distal end of the flexible coil. The deflection of the distal end of the coil just as the jaws are about to close on a tissue to be sampled often displaces the jaws relative to the tissue to be sampled and results in a failure to acquire the sample or the acquisition of an undesired sample. Therefore, in the case of biopsy forceps, it is desirable to stiffen the distal portion of the coil to prevent it from deflecting when the jaws are being closed.

Co-assigned U.S. Pat. No. 5,228,451 to Bales et al. discloses a biopsy forceps device having a stiff distal portion. The distal portion of the flexible coil is made stiff by wrapping it with a stiffening sleeve which extends for several inches along the coil and covers a portion of the clevis. While the sleeve advantageously stiffens the distal portion of the coil, it also increases the outer diameter of the coil and provides an uneven surface. The increased diameter of the coil at the location of the sleeve is can hinder the travel of the coil through the narrow lumen of the endoscope. The uneven surface of the coil can also possibly cause undue wear or damage to the inner surface of the endoscope lumen.

Biopsy scraping tools, on the other hand, rely on the ability of the distal end of the coil to flex. Although the coil is generally flexible throughout its length, in a biopsy scraping tool, it is desirable to provide added flexibility at the distal end of the coil. U.S. Pat. No. 4,936,312 to Tsukagoshi shows a flexible body cavity inserting instrument which is a biopsy scraping tool. The tool has a long flexible coil attached at its proximal end to an actuation handle and one or more control wires which extend from the actuation handle through the coil to the distal end of the coil. The distal end of the control wire is coupled to a part of the distal end of the coil or the end effector so that pulling on the control wire causes the distal end of the coil to flex like a finger. A resilient member at the distal end of the coil returns the coil to a straightened position when tension on the control wire is released. A scraping end effector such as a brush or a cup with a sharp edge is fixedly attached to the distal end of the coil. To take a biopsy sample, the scraping end effector is positioned up against a tissue to be sampled and the actuating handle is manipulated to cause the distal end of the coil to flex. The flexing of the distal end of the coil causes the scraping end effector to move across the surface of the tissue to be sampled and to scrape off a sample. Tsukagoshi enhances the flexibility of the coil's distal end by providing the coil with a loosely wound distal end. At the distal end of the coil, the spirals forming the coil are spaced farther apart than the remainder of the coil which is closely wound with the spirals of the coil close together. The enhanced flexibility of the distal end allows it to bend up to 180 degrees which, in addition to enhancing the efficacy of the scraping end effector, also allows the tool to be bent to sample tissues which cannot be reached by an endoscope.

It is apparent, therefore, that in flexible surgical instruments having hollow lumen flexible coils, it is sometimes desirable to stiffen the distal portion of the coil and it is sometimes desirable to enhance the flexibility of the distal portion of the coil. Unfortunately, the known methods of altering the flexibility of the distal portion of the coil each have significant drawbacks. Moreover, the manufacturing procedures used to enhance the flexibility of the distal portion of the coil are so different from those used to stiffen the distal portion of the coil that the coils cannot be manufactured with the same machines. In addition, it is often desirable to stiffen the proximal portion of the coil to prevent buckling of the coil when the coil is inserted through an endoscope.

SUMMARY OF THE INVENTION

It is therefore an object of the invention to provide a hollow lumen coil for a surgical instrument where a portion of the coil can be made stiff without increasing its outer diameter.

It is another object of the invention to provide a hollow lumen coil for a surgical instrument where a portion of the coil can be made stiff without compromising the smoothness of the outer surface of the coil.

It is also an object of this invention to provide a hollow lumen coil for a surgical instrument where a portion of the coil can be made more flexible without requiring complicated manufacturing procedures.

It is yet another object of this invention to provide a hollow lumen coil for a surgical instrument where a portion of the coil can be either stiffened or made more flexible through the use of similar manufacturing procedures.

In accord with these objects which will be discussed in detail below, the hollow lumen coil for a surgical instrument according to the invention is made from a continuous helically wound filament which is wound with at least two different preload tension at different portions of the coil. When a relatively high preload tension is applied to the filament as the coil is wound, the coil will be relatively stiff. When a relatively low preload tension is applied to the filament as the coil is wound, the coil will be relatively flexible. By changing the preload tension applied to the filament while winding the coil, the coil is provided with areas of different stiffness and flexibility. The preload tension may be varied gradually or abruptly and may be varied several times along the length of the coil.

Additional objects and advantages of the invention will become apparent to those skilled in the art upon reference to the detailed description taken in conjunction with the provided figures.

BRIEF DESCRIPTION OF THE DRAWINGS

FIG. 4 is a broken side elevation view, partly in section and partly transparent, of a surgical instrument incorporating a coil according to the invention and having biopsy forceps end effectors;

FIG. 5 is a broken longitudinal sectional view of a biopsy scraping tool end effector coupled to the distal end of a coil according to the invention; and FIG. 6 is a view similar to FIG. 5 showing the distal end of the coil flexed approximately 180 degrees.

DETAILED DESCRIPTION OF THE PREFERRED EMBODIMENTS

Figure 1:
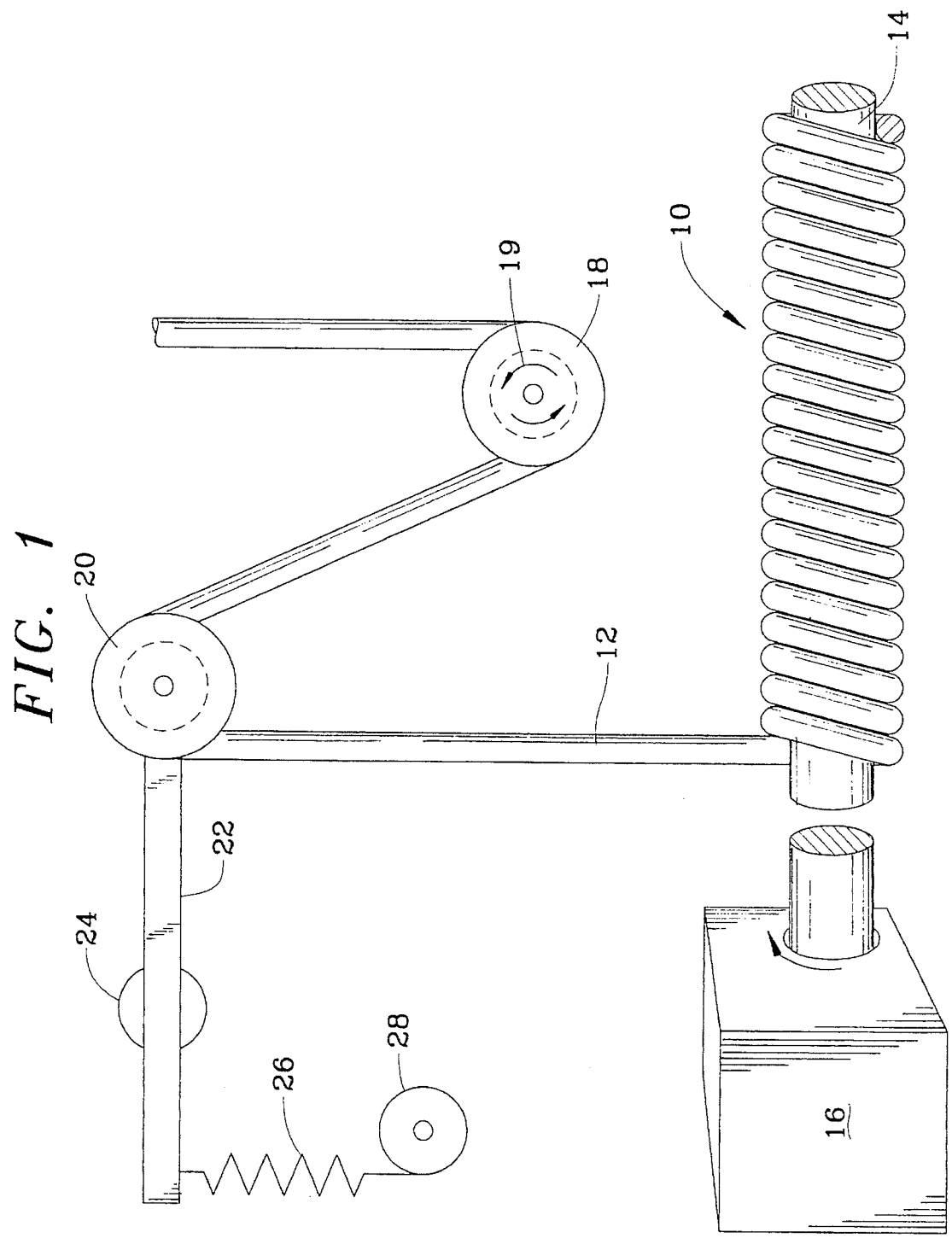
FIG. 1 is a schematic side elevation view of a coil winding device for making hollow lumen coils according to the invention.

Referring now to FIG. 1, a hollow lumen coil 10 for use in a surgical instrument according to the invention is made from a steel filament 12 which is wound around a mandrel 14. The mandrel 14 is rotated by a motor 16 and the filament 12 is fed from a supply (not shown) to the mandrel 14 by a main tension pulley 18 and a cantilevered pulley 20. The mandrel 14 need only be a few inches longer than the coil and is preferably held by two chucks (not shown), one at either end. The coil 10 is removed from the mandrel 14 by removing one of the chucks and pulling the coil off the mandrel. The main tension pulley 18 is provided with a braking mechanism 19 which applies a selectable braking torque to the pulley 18 which effects a certain tension in the filament 12 between the pulley 18 and the mandrel 14. The cantilevered pulley 20 is mounted on one end of a lever 22 having a fulcrum 24. The other end of the lever 22 is coupled to an adjustable spring 26. The force of the 26 is adjusted by an adjusting knob 28 which stretches the 26 to increase the force on the lever 22 according the Hooke's Law ($F=-kx$, where k is a constant for the spring and x is the distance the spring is stretched). The farther the spring 26 is stretched, the greater the force applied to the lever 22. The force applied to the lever 22 is transmitted to the pulley 20 via the fulcrum 24 and thus to the portions of the filament 12 between the pulley 20 and the pulley 18 and between the pulley 20 and the mandrel 14. The force which is applied to the filament 12 as it is wound around the mandrel 14 is called the "preload tension". In accord with the invention, the higher the preload tension applied to the filament 12, the stiffer the coil 10 will be. Conversely, the lower the preload tension, the more flexible the coil 10 will be. It is an important aspect of the invention, however, that the preload tension be changed at least once during the coil winding process. Using an apparatus like the one shown in FIG. 1, the preload tension may be changed by changing the braking torque on the pulley 18, by changing the spring force applied to the lever 22, or by a combination of both. The coil is preferably made from stainless steel Type 304 wire filament having a diameter of approximately 0.021 inches and is wound with tensions preferably ranging from nil to several pounds.

From the foregoing, those skilled in the art will appreciate that the apparatus schematically illustrated in FIG. 1 is merely illustrative of the principles of the invention and that many different kinds of apparatus may be adapted to perform the method of the invention and make the coil of the invention. As mentioned above, the essence of the invention is that the preload tension on the filament is changed at least once during the winding of the coil so that the coil is provided with at least two portions of different flexibility/stiffness.

Figure 2:
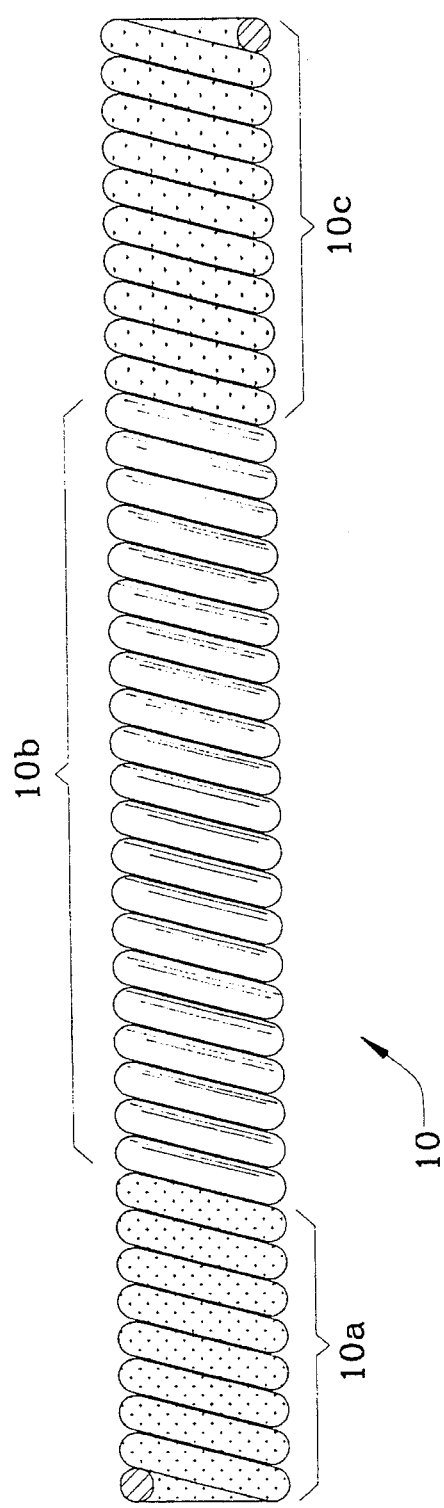
FIG. 2 is a schematic side elevation view of a coil according to the invention having a relatively stiff proximal end portion, a moderately flexible middle portion, and a highly flexible distal end portion.
Figure 3:
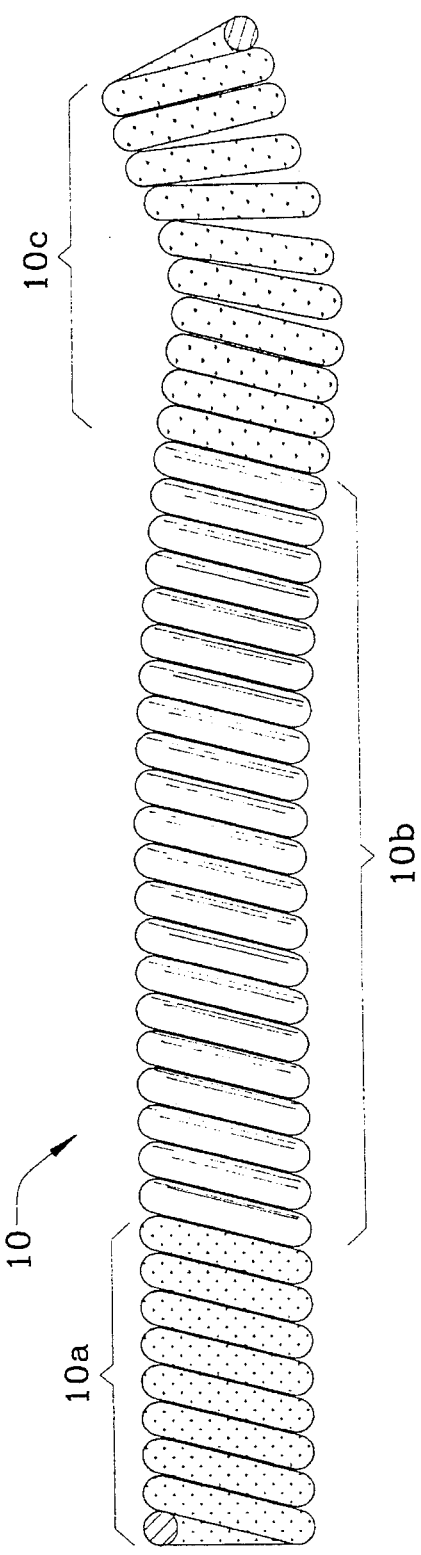
FIG. 3 is a view of the coil of FIG. 2 illustrating the relative stiffness of the three portions of the coil.

FIGS. 2 and 3 show the coil 10 where a proximal portion 10a has been wound with a relatively high preload tension, a middle portion 10b has been wound with a moderate preload tension, and a distal portion 10c has been wound with a relatively low preload tension. FIG. 3 illustrates how the preload tension affects the flexibility/stiffness of the coil. As seen in FIG. 3, the portion 10a, having a high preload tension, is not bent at all, indicating relative stiffness of this portion. The portion 10b, having a moderate preload tension, is bent slightly, indicating moderate flexibility of the coil. The portion 10c, having a low preload tension, is bent significantly, indicating a relatively high flexibility.

A typical coil, according to the invention, will have a length of several feet and an outer diameter of about one sixteenth of an inch. A single filament coil may have approximately forty to fifty turns per inch. Unlike some prior art coils, the coils according to the invention are uniformly wound with the same number of turns per inch throughout the length of the coil. It will also be appreciated that coils according to the invention may be wound from a single filament or from several filaments wound parallel to each other.

FIG. 4 shows a typical endoscopic biopsy forceps surgical instrument 30 incorporating the coil 10 according to the invention. The instrument 30 generally includes a handle 32 coupled to the proximal end of the coil 10 and one or more end effectors 34 coupled to the distal end of the coil 10. The handle 32 includes a central shaft 36 and a displaceable spool 38. The proximal end of the shaft 36 is provided with a thumb ring 40 and a longitudinal bore 42 is provided at the distal end of the shaft 36. A longitudinal slot 44 extends from the proximal end of bore 42 to a point distal of the thumb ring 40. The displaceable spool 38 is provided with a cross member 46 which passes through the slot 44 in the central shaft 36. One or more control wires 48 extend through the coil 10 and are coupled at their proximal end(s) to the cross member 46. The distal end(s) of the control wire(s) are coupled to the end effector(s) 34. Relative movement of the shaft 36 and spool 38 results in movement of the control wire(s) 48 relative to the coil 10. Such action results in actuation of the end effector 34. As shown in FIG. 4, the end effectors 34 are biopsy forceps jaws and the operation of the instrument is substantially the same as described in co-assigned U.S. Pat. No. 5,228,451 to Bales et al. In this biopsy forceps instrument, it is usually advantageous to enhance the stiffness of the coil 10 at both the proximal portion 10a and the distal portion 10c relative to the middle portion 10b. Enhanced stiffness at the distal portion 10c prevents the distal portion of the coil from deflecting when the forceps jaws are closed. Enhanced stiffness at the proximal portion 10a of the coil relieves strain limiting twist and movement of the coil relative to the shaft 36 so that the coil 10 does not bend sharply at the distal end of the shaft 36.

FIGS. 5 and 6 show the distal portion 10c of coil 10 with a biopsy scraping brush end effector 54 attached thereto. The proximal portion of this instrument may be substantially the same as the proximal portion of the instrument shown in FIG. 4. The brush end effector 54 is substantially the same as the brush disclosed in U.S. Pat. No. 4,936,312 to Tsukagoshi. In this type of instrument, the brush 54 is fixed to the distal end of the coil 10 by brazing or the like. A single control wire 58, which is coupled to the cross member 46 of the spool 38 extends into the coil 10 and terminates proximal of the brush 54. A bending member 60 is attached to the distal end of the control wire 58 and is attached to the coil 10 at a point proximal of the distal end of the control wire 58. When the control wire 58 is pulled in the proximal direction, the bending member 60 is bent by the control wire 58. When the bending member 60 is bent, as shown in FIG. 6, the distal portion 10a of the coil 10 bends to follow the bending member 60. In this biopsy scraping instrument, it is usually advantageous to enhance the flexibility of the coil 10 at the distal portion 10c.

There has been described and illustrated herein a hollow lumen coil for surgical instruments, methods for making the coil, and surgical instruments incorporating the coil. While particular embodiments of the invention have been described, it is not intended that the invention be limited thereto, as it is intended that the invention be as broad in scope as the art will allow and that the specification be read likewise. Thus, while a particular apparatus for performing the method of making the coil of the invention has been disclosed, it will be appreciated that other apparatus could be utilized. Also, while steel filament coils have been shown, it will be recognized that other types of filaments could be used with similar results obtained. Moreover, while typical dimensions have been disclosed in reference to the coil, it will be appreciated that other dimensions could be used as well. Furthermore, which specific surgical instruments incorporating the coil have been shown, it will be understood that the coil may be used in other surgical instruments where enhanced stiffness and/or flexibility of a portion of the coil is advantageous. It will therefore be appreciated by those skilled in the art that yet other modifications could be made to the provided invention without deviating from its spirit and scope as so claimed.

I claim:

1. A surgical instrument, comprising:
   a) a helically wound continuous filament hollow lumen coil wherein said filament is wound with a first preload tension for a first number of turns and wound with a second preload tension for a second number of turns, said second preload tension being different from said first preload tension;
   b) a proximal handle coupled to a proximal end of said coil; and
   c) a distal end effector coupled to a distal end of said coil.

2. A surgical instrument according to claim 1, further comprising:
   d) a control wire extending through said coil, a proximal end of said control wire being coupled to said proximal handle and a distal end of said control wire being coupled to said end effector.

3. A surgical instrument according to claim 2, wherein:
   said handle includes a central shaft and a displaceable spool, said proximal end of said coil being coupled to said central shaft and said proximal end of said control wire being coupled to said displaceable spool.

4. A surgical instrument according to claim 3, wherein:
   said distal end effector comprises a pair of biopsy forceps jaws.

5. A surgical instrument according to claim 4, wherein:
   said second preload tension is greater than said first preload tension, and said second number of turns are at a distal portion of said coil.

6. A surgical instrument according to claim 5, wherein:
   said filament is also wound with a third preload tension for a third number of turns, said third preload tension being greater than said first preload tension, and third number of turns being at a proximal portion of said coil.

7. A surgical instrument according to claim 3, wherein:
   said distal end effector comprises a biopsy scraping brush.

8. A surgical instrument according to claim 7, wherein:
   said second preload tension is less than said first preload tension, and said second number of turns are at a distal portion of said coil.

* * * * *